United States Patent
Tajima et al.

(10) Patent No.: US 6,402,737 B1
(45) Date of Patent: Jun. 11, 2002

(54) SURGICAL APPARATUS

(75) Inventors: Fujio Tajima, Tsuchiura; Kazutoshi Kan; Yasuhiro Nemoto, both of Ibaraki-ken; Masakatsu Fujie, Ushiku, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/272,784

(22) Filed: Mar. 19, 1999

(30) Foreign Application Priority Data

Mar. 19, 1998 (JP) .......................................... 10-069790

(51) Int. Cl.[7] .............................................. A61B 17/00
(52) U.S. Cl. .............................. 606/1; 606/10; 606/13; 606/41; 345/700; 345/740; 345/745
(58) Field of Search ................................. 606/1, 10, 11, 606/41, 42, 129, 130, 12, 38, 32–35; 345/740, 745, 433, 4, 329, 501–505, 30, 700–703, 717, 727, 747; 600/407, 427

(56) References Cited

U.S. PATENT DOCUMENTS

| | | | | |
|---|---|---|---|---|
| 5,049,147 A | * | 9/1991 | Danon .......................... 606/10 |
| 5,098,426 A | * | 3/1992 | Sklar et al. ...................... 606/5 |
| 5,305,203 A | * | 4/1994 | Raab ...................... 364/413.13 |
| 5,395,356 A | * | 3/1995 | King et al. ...................... 606/4 |
| 5,464,013 A | * | 11/1995 | Lemelson ................. 128/653.1 |
| 5,537,618 A | * | 7/1996 | Boulton et al. ............. 395/161 |
| 5,620,608 A | * | 4/1997 | Rosa et al. ................. 210/739 |
| 5,748,767 A | * | 5/1998 | Raab ........................... 382/128 |
| 5,820,627 A | * | 10/1998 | Rosen et al. ................... 606/15 |
| 5,855,553 A | | 1/1999 | Tajima |
| 5,868,728 A | * | 2/1999 | Giungo et al. .................. 606/1 |
| 5,910,139 A | * | 6/1999 | Cochran et al. ................ 606/1 |
| 5,938,655 A | * | 8/1999 | Bisch et al. .................... 606/1 |
| 5,964,746 A | * | 10/1999 | McCary ......................... 606/1 |
| 5,968,035 A | * | 10/1999 | Goodman et al. ............. 606/12 |
| 5,976,122 A | * | 11/1999 | Madhani et al. ............... 606/1 |
| 6,004,314 A | * | 12/1999 | Wei et al. ...................... 606/12 |
| 6,011,563 A | * | 1/2000 | Fournier et al. ............ 345/500 |
| 6,063,075 A | * | 5/2000 | Mihori ......................... 606/35 |
| 2001/0016696 A1 | * | 8/2001 | Bystrom et al. .............. 601/41 |
| 2001/0032085 A1 | * | 10/2001 | Goedeke et al. ............ 704/275 |

* cited by examiner

Primary Examiner—Linda C. M. Dvorak
Assistant Examiner—A. Farah
(74) Attorney, Agent, or Firm—Antonelli, Terry, Stout & Kraus, LLP

(57) ABSTRACT

A surgical apparatus for automatically and dynamically changing the constitution of a system and the operation of respective elements. The surgical apparatus includes a plurality of devices respectively, a supervisory controller having a transmission path among the plurality of devices for supervisorily controlling the devices and an operational procedure description store for storing an operational procedure description describing operational procedures of the plurality of devices in which the supervisory controller includes a detector for detecting constitutions of the devices and for transmitting the operational procedure description necessary for the devices detected by the detector to the respective devices via the transmission path.

11 Claims, 14 Drawing Sheets

SURGICAL APPARATUS

BACKGROUND OF THE INVENTION

1. Field of the Invention

The present invention relates to a medical instrument, particularly to a surgical apparatus for supporting a surgical operator in carrying out medical treatment on a diseased part.

2. Description of Related Art

Conventionally, there has been a manipulator system for surgical treatment described in JP-A-08-071072 as an apparatus for supporting surgery. In the system, there is installed a manipulator for surgery for carrying out observation and treatment of an in vivo tissue portion, manipulating means for handling the manipulator for surgery, controlling means for controlling operation of the, manipulator for surgery based on manipulation data from the manipulating means and parameter variable means capable of arbitrarily changing control parameters necessary for carrying out operational control of the manipulator for surgery. According to the constitution, the control parameters can be changed to a state which is easy to manipulate for a surgical operator, promotion of manipulating performance can be achieved, particularly, when the control parameters are changed during surgical operation, various manipulation can be carried out and a variation in the manipulation is enlarged.

In actual surgical operation, the constitution of a surgical apparatus needs to change in accordance with a difference in users and a difference in cases. Further, such a need can be caused even at a site of operation where surgical operation is in progress. For example, it is necessary to change system constitution such as increasing or decreasing a number of operational manipulators adaptively to circumstances in accordance with a difference in cases or a situation of a site of operation or changing measuring instruments used.

When the system constitution, for example, a constitution in devices such as, for example, operational manipulators is changed as described above, or, conversely, when different operation is carried out while the same system constitution or the same constituent elements remain as they are, naturally, unless description of a procedure for operating these, that is, operational control program per se for each element is changed, function of the element and accordingly, that of a total of the apparatus cannot be achieved or there may produce a possibility in which the treatment cannot be continued depending on cases. For example, an operational control program of a manipulator for incising a diseased part and that of a manipulator for positioning a suction tube naturally differ from each other and even with the same manipulator for incision, in the case of incision by laser beam, positioning control of a tip of an apparatus becomes important since it is brought into a noncontact state in respect of the diseased part, however, when incision by mechanical force, that is, incision by using a scalpel is carried out, the scalpel is brought into contact with the diseased part and accordingly, the above-described positioning control cannot be operated correctly and therefore, an operational control program described based on an algorithm of force control different therefrom is needed. However, conventionally, such a program per se is not changed dynamically and automatically and the operation is persistently dependent on instruction of a user.

Further, in the conventional art, there is no notion of or authentication of a user and a surgical apparatus cannot be informed of who is a current user. Therefore, setting of apparatus inherent to a user needs to carry out by the user per se. Further, a person who is not a proper user cannot be prevented from using a surgical apparatus.

SUMMARY OF THE INVENTION

It is an object of the invention to provide a surgical apparatus for automatically and dynamically changing a constitution of a system and operation of respective elements.

In order to achieve the above-described object, according to an aspect of the invention, there is provided a surgical apparatus used in a surgical operation, the surgical apparatus comprising devices having controlling means, supervisory controlling means having communicating means among the devices, and operational procedure description storing means for storing an operational procedure description describing operational procedures of the devices, wherein the supervisory controlling means includes detecting means for detecting constitutions of the devices and transmits the operational procedure description in conformity with the constitutions of the devices detected by the detecting means to the respective devices by the communicating means.

In order to achieve the above-described object, according to other aspect of the invention, there is provided a surgical apparatus comprising a plurality of devices respectively having controlling means including devices comprising operational manipulators for operating tools used in a surgical operation, operational instruction inputting means for instructing operations of the devices for operating the tools, supervisory controlling means having communicating means among the plurality of devices for generally controlling the devices, and operational procedure description storing means for storing an operational procedure description describing operational procedures of the plurality of devices, wherein the supervisory controlling means includes detecting means for detecting constitutions of the devices and transmits the operational procedure description in conformity with the constitutions of the devices detected by the detecting means to the respective devices by the communicating means.

The above-described detecting means may detect presence or absence of use of the devices, tools provided to the devices and/or content of operation of the devices as the constitutions of the devices.

Further, the above-described detecting means may detect the constitutions of the devices by request from the side of the devices to the supervisory controlling means by interruption when a power source is inputted to the surgical apparatus or the surgical apparatus is reset.

Further, the above-described detecting means may detect the constitutions of the devices by request from the devices to the supervisory controlling means by interruption when there causes a change in the constitutions of the devices.

According to the surgical apparatus, the constitutions of the devices are automatically and dynamically detected by the supervisory controlling means, operational procedure description can be set to the devices and accordingly, the system constitution and the constitutions and the operation of the devices can be changed automatically and dynamically. Thereby, an error in view of software of transmitting erroneous operational procedure description to the devices can be prevented and further, an error in view of hardware in the constitutions of the devices can be discovered beforehand. Particularly, the surgical operators are not troubled with various settings while the surgical operation is in progress which is effective in preventing erroneous setting.

Further, an operational procedure description of default may be provided to the devices and when the operational procedure description is not transmitted from the supervisory controlling means, the devices may execute the operational procedure description of default. Thereby, a minimum processing can continuously be executed and emergency measure becomes feasible.

Further, authenticating means for authenticating the users may be provided and priorities of use of the devices in respect of a plurality of users may be set by the supervisory controlling means. Thereby, the surgical operation can firmly be shared by the plurality of surgical operators and a high degree of the surgical operation can be carried out. Further, by providing the authenticating means, the supervisory controlling means automatically determines the users and can set the operational procedure description exclusive for the users to the devices.

Further, authenticating means for authenticating the users may be prepared, the supervisory controlling means may determine the priorities provided to the plurality of users in respect of using the devices and the operational procedure description prepared for one of the users having the highest priority may be transmitted to the device. Thereby, the operation of the devices becomes easy to handle by the users.

Further, there may be provided means having data in respect of a constitution of a device of default with regard to a case for presenting a difference between the constitution of the device of default and the constitution of an actually set device. Thereby, an error in the constitution of the device becomes easy to discover and the surgical operators can be supported by presenting data with regard to the above device constitution.

DESCRIPTION OF THE PREFERRED EMBODIMENT

Figure 1:
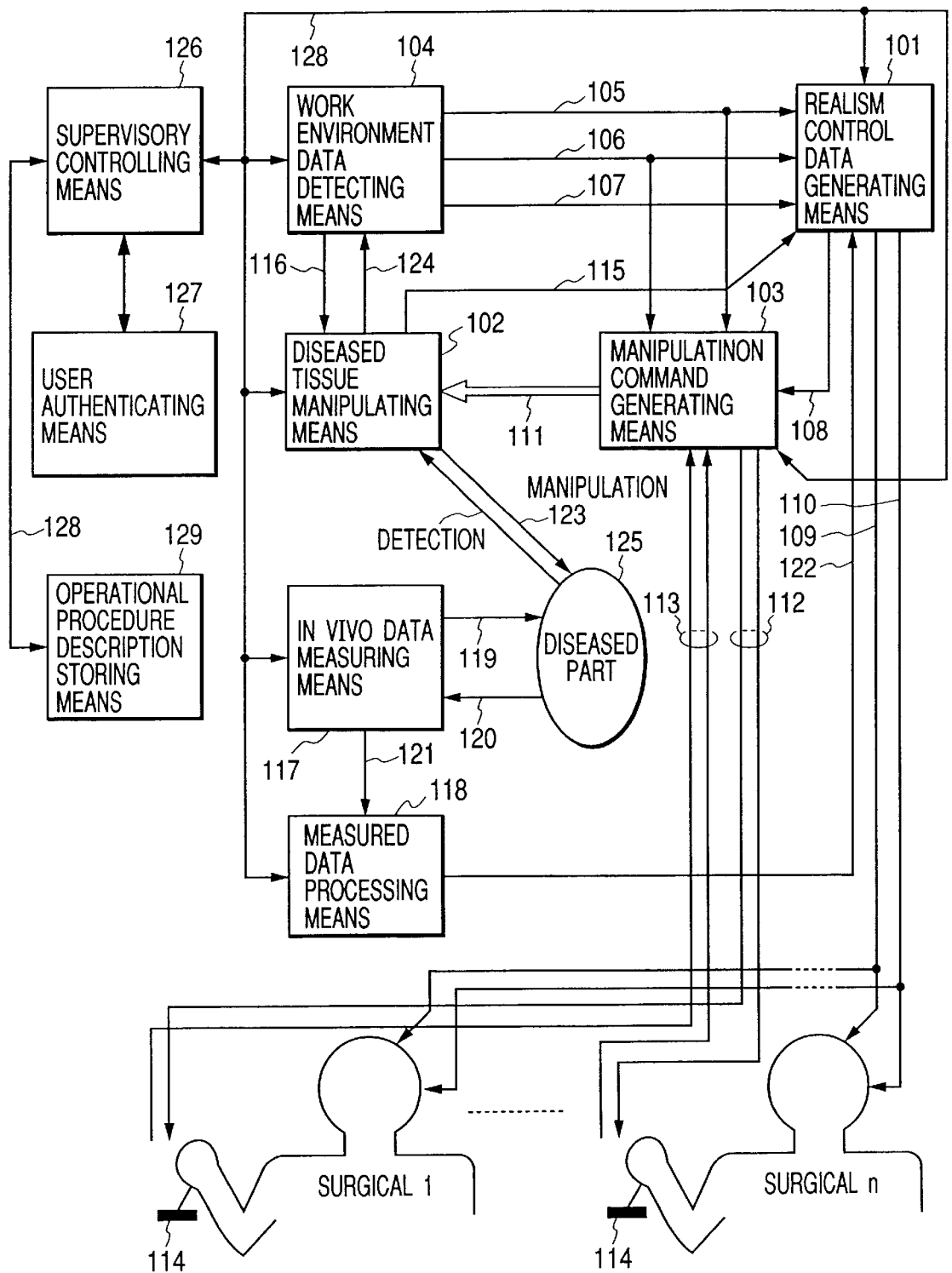
FIG. 1 is a constitution diagram of an embodiment of the invention.

FIG. 1 shows a constitution of an embodiment according to the invention.

In FIG. 1, numeral 101 designates realism control data generating means including devices of a display, a monitoring device, a speaker and the like and giving a realistic feeling to a surgical operator, numeral 102 designates diseased tissue manipulating means comprising slave manipulators including treatment instruments (tools) of a scalpel, optical fiber laser, a pipe for injecting physiological salt water and so on, numeral 103 designates manipulation command generating means constituting control devices of master and slave manipulators, numeral 104 designates work environment data detecting means including a force sensor, a proximity sensor, a visual sensor (image taking means, television camera) and the like, numeral 117 designates in vivo data measuring means constituted by including an MRI (Magnetic Resonance Imager), a CT (Computed Tomography), an ultrasonic wave scanner and the like, numeral 118 designates measured data processing means constituted by computers for image processing, numeral 119 designates an input signal for measuring an in vivo portion, numeral 120 designates an output signal transmitted through or reflected by the in vivo portion, numeral 121 designates measure data of the in vivo portion, numeral 122 designates in vivo data which is visualized and reconstructed in 3D (Dimension), numeral 123 designates manipulation which is carried out by the diseased tissue manipulating means, numeral 124 designates detected data by various sensors constituting portions of the work environment data detecting means, numeral 125 designates a diseased part, numeral 105 designates force sensor data, numeral 106 designates proximity sensor data, numeral 107 designates visual sensor data, numeral 108 designates virtual force reflection data, numeral 109 designates a processed and synthesized image, numeral 110 designates a virtual sound field, numeral 111 designates manipulation command data, numeral 112 designates synthesized force reflection, numeral 113 designates action command, numeral 114 designates motion command inputting means, numeral 115 designates slave manipulator tip position data, numeral 116 designates magnification ratio data, numeral 126 designates supervisory controlling means for generally controlling the above-described respective means (devices) (control device having an order higher than those of respective devices), numeral 127 designates user authenticating means including an input device of an IC (Integrated Circuit) card reader or the like, numeral 128 designates a transmission path constituted by a network or an exclusive communication network and numeral 129 designates operational procedure description storing means constituted by storing means such as a magnetic disk device.

The work environment data detecting means 104 is provided with sensor portions at a tip and a periphery of a slave manipulator which is a constituent element of the diseased tissue manipulating means 102 and detects the diseased part and its surrounding environment by the visual sensor and the force sensor and the proximity sensor at the tip of the manipulator.

The realism control data generating means 101 modifies and synthesizes data detected by the work environment data detecting means 104, three-dimensional reconstructed image data of the in vivo portion outputted from the measured data processing means 118 and the slave manipulator tip position information 115 and forms image, sound and virtual force reflection. Thereby, a state of the diseased portion is shown to one or more surgical operators.

Data of the force sensor and the proximity sensor are also transmitted to the manipulation command generating mean 103. Actual reactive force detected by the force sensor is converted into a range capable of being sensed by respective surgical operators.

The virtual force reflection 108 formed by the realism control data generating means 101 is added with actual reactive force the range of which has been converted and operational force of other surgical operator and is conveyed to the respective surgical operators via the motion command inputting means 114. The respective surgical operators input the action command 113 to the diseased tissue manipulating means 102 via the motion command inputting means 114 based on data shown by the realism control data generating means 101. The inputted action command 113 is converted into the manipulation command data 111 by the manipulation command generating means 103. The diseased tissue manipulating means 102 interprets and executes the manipulation command data 111 with the magnification ratio data 116 as parameters and manipulates the diseased tissue.

At this occasion, simultaneously, the in vivo data measuring means 117 inputs measuring signals to the diseased part 125 at every constant period of time and catches the output signal transmitted therethrough or reflected thereby. The signal is digitized and transmitted to the measured data processing means 118 as measured data.

The measure data processing means 118 calculates the measured data provided at every constant period of time and reconstructs the result as three-dimensional image data.

The supervisory controlling means 126 grasps a current user and specific constitutions of the respective means in respect of the above-described respective means and monitors operational situations of the respective means after distributing description of necessary operational procedure (hereinafter, program). When a change in the constitution of each means (interchange, addition, removal of device or tool) is detected, the supervisory controlling means 126 updates data for control (hereinafter, device table) in accordance with an identification number (hereinafter, device ID) informed from each means. Further, when a change in the user (new start of use, finish of use or the like) is detected, the supervisory controlling means 126 redistributes a program to each device currently registered in the device table to rearrange environment of use inherent to the user. Or, also when a change in content of operation is informed from each means by the users, the supervisory controlling means 126 redistributes the program as mentioned above. In this case, there also are prepared a user table and a device table of default as well as a program of default for each means and when a specific user does not use the apparatus or when authenticating of the user is failed by some reason, or when data from the operational procedure description storing means is failed to output, the supervisory controlling means 126 carries out setting and control of each means by using each table and the program of default. By using the program of default, minimum action can be compensated for and emergency measure can be carried out.

A user declares that the user uses the apparatus via the user authenticating means 127. The supervisory controlling means 126 registers an identifier (hereinafter, user ID) of the user to data for controlling the user (hereinafter, user table). In this case, the user is not limited to one person but a plurality of users can use the respective means of the apparatus commonly or dividedly.

The transmission path 128 is a medium for connecting the supervisory controlling means 126 and other respective means and transmitting necessary data. This is realized by a bus prescription of a computer including interruption lines such as IEEE1073, IEEE1014 or the like or a computer network represented by CSMA/CD system prescribed in IEEE802,3. Or, this is mountable by an industrial small-scale network, for example, one based on prescription of ISO11898 or the like.

The operational procedure description storing means 129 is stored with the above-described programs and a user register list.

Next, an explanation will be given of basic constitutions of respective means in reference to FIG. 2. A large rectangle 200 on the lower side of the drawing represents the respective means.

Numeral 201 designates operational procedure description interpreting and executing means, numeral 202 designates operational procedure description recording and storing means, numeral 203 designates default operational procedure description storing means, numeral 204 designates a mechanism unit of the respective means and numeral 205 designates an inner transmission path. As specific mounted devices for portions 201 through 205, it is conceivable that numeral 201 designates a microprocessor, numeral 202 designates a static RAM (Random Access Memory) and numeral 203 designates ROM (Read Only Memory). Further, numeral 204 designates a master and slave manipulator mechanism unit, various image measuring apparatus (MRI, CT, ultrasonic wave scanner, etc.), an image processing apparatus, an image and voice presenting apparatus, an optical image and reconstructed image synthesizing apparatus for forming or synthesizing content of presentation, a sensor data modality converting apparatus, a virtual sound field forming apparatus, a work environment data detecting apparatus such as a television camera, a force sensor, a proximity sensor or the like or an apparatus of interpreting and converting action command from an operation input unit. Numeral 205 designates address bus and data bus. Further, an intermediary between portions 201 and 204 is frequently connected by a path referred to as an outside bus. It may be, for example, a bus the specification of which is publicly laid open or it may be mounted with an original specification.

Figure 2:
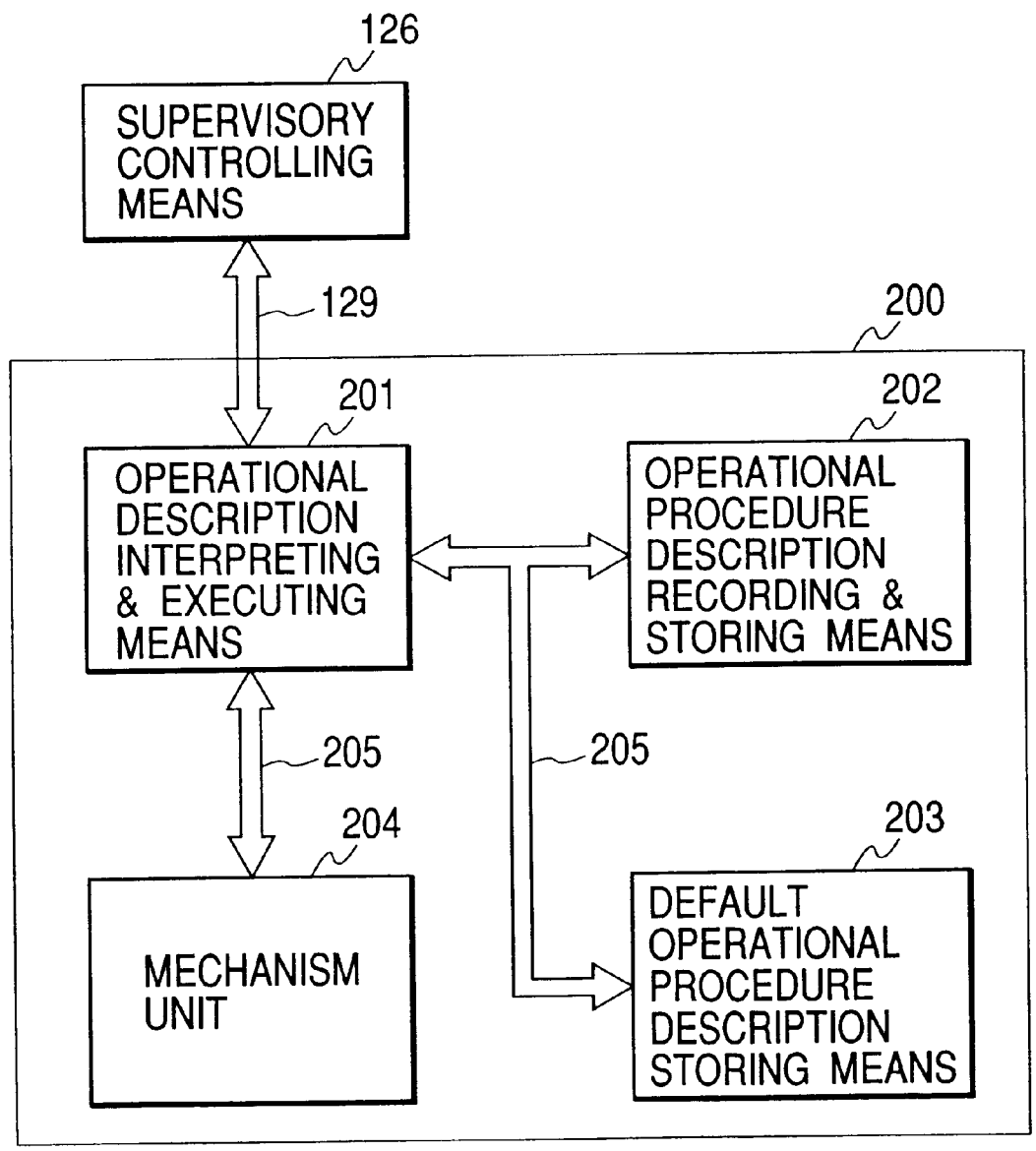
FIG. 2 is a basic constitution diagram of respective means.
Figure 3:
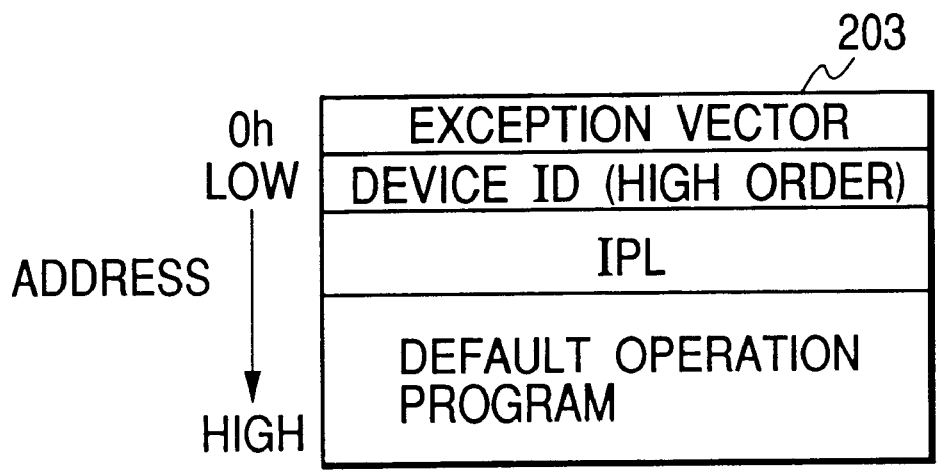
FIG. 3 is a diagram showing an embodiment of a memory map of ROM.

FIG. 3 shows an example of a memory map of ROM 203 of FIG. 2. ROM 203 is stored with exception vector, an upper portion of device ID, mentioned later, IPL (initial program loader) and a default operation program from lower of the address. The exception vector signifies a table of addresses in which when an exception is caused in executing a program of the means, there are described processings in accordance with the kind of the exception. Normally, resetting of a processor is regarded as an exception and a front address of an operational program in rise of the program is recorded at the front of the vector. In this case, a front address of IPL mentioned above corresponds thereto. The device ID signifies an identifier or an identifying number for identifying a device which is actually used in each means. In this case, data for identifying the class of the device is recorded at a portion constituting a higher order. For example, ordinal numbers are defined such as a manipulator for operation is at first, an image measuring apparatus is at second and an operational input apparatus is at third. This may naturally be expressed not by a number but by name or the like since it is for identification. Further, expression of class is used since there are various kinds in the manipulators for operation and the image measuring apparatus. In order to actually identify the only device, identifiers indicating a kind of tool and a kind of operation are separately acquired at a middle order and a lower order of the device ID and data summarizing these are informed to the supervisory controlling means 126 as a device ID of a certain means. A description will be given later in respect of IDs at the middle order and the lower order, a method of acquiring these and a procedure of notifying them to the supervisory controlling means. A step which is executed in resetting as mentioned above is IPL (Initial Program Loader). IPL is stored with a program describing a procedure of communicating with the supervisory controlling means 126 and acquiring an operational program. Each means executes a necessary procedure in accordance with the description of IPL when it is started or restarted for some reason. The default operation program is used when each means is failed to communicate with the supervisory controlling means 126 at rise of the program for some reason (malfunction of transmission path, failure of the supervisory controlling means 126, and the like). When an operational program is failed to acquire as mentioned later, a program of this portion is executed and each means guarantees a function of itself for the time being.

Figure 4:
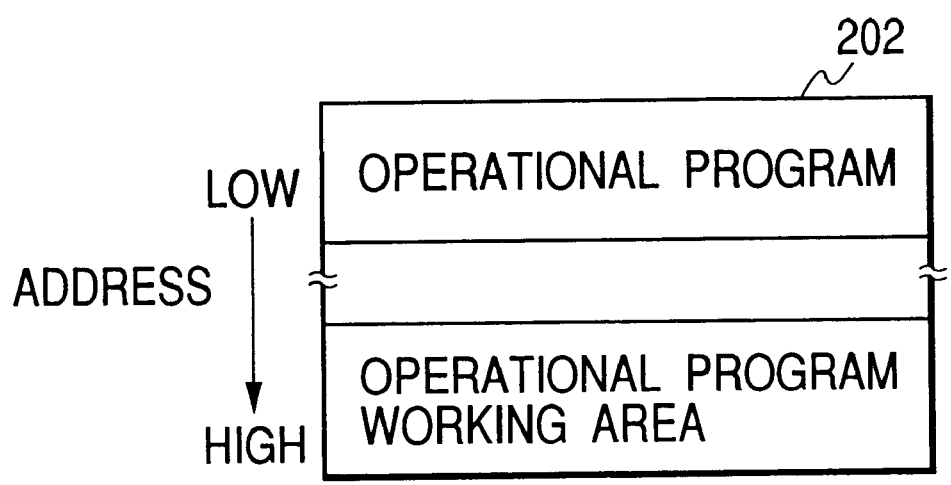
FIG. 4 is a diagram showing an embodiment of a memory map of RAM.

FIG. 4 shows an example of a memory map of RAM in FIG. 2. RAM 202 is stored with an operation program acquired in executing IPL which is executed from its front portion. Further, a working area necessary in executing the program is also provided therein. A non-volatile one is used in RAM 202 and accordingly, for example, even in restarting operation after cutting a power source, data in an operation before restarting can be reutilized when memory allocation in program operation is carried out by a method in which the allocation can be traced such that the allocation is executed always at the same address.

Figure 5:
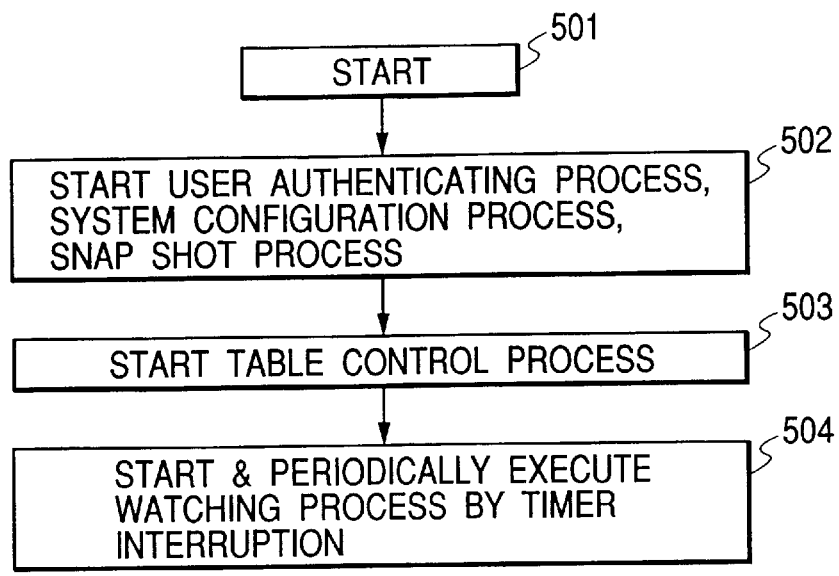
FIG. 5 is a diagram showing an operational procedure of supervisory controlling means.

Next, an explanation will be given of an operational procedure of the supervisory controlling means 126 in reference to FIG. 5.

It is simple for an example of actually mounting the supervisory controlling means 126 to utilize an operating system (hereinafter, OS) for supporting multiple users and real time multiple processes. First, OS in the means is started by making ON a power source or resetting it, (step 501). Next, a user authenticating process, a system configuration process and a snap shot process are created and executed (step 502). A table control process for controlling a user table and a device table is started after carrying out communication with respective means and obtaining required data at step 502 (step 503). Further, a watch dog process for monitoring operational states of the respective means is started and is periodically executed by timer interruption (step 504). The series of procedures are described in a file executed at rise of operation and are automatically executed. The user table and the device table are placed in a shared memory and all of processes connected thereto can be referred. However, what can write on it is only the table control process, mentioned later. Prohibition of writing by other process can be realized by intervention of OS.

Figure 6:
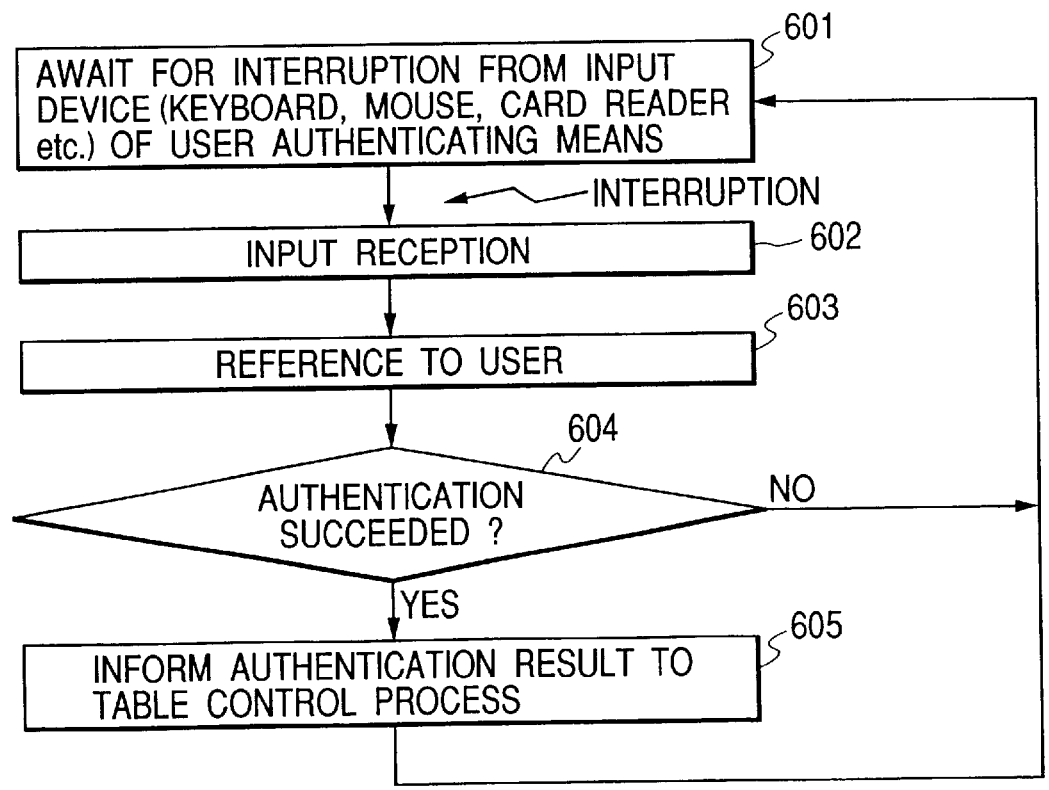
FIG. 6 is a diagram showing an operational procedure of user authenticating process.

FIG. 6 shows an operational procedure of the user authenticating process.

The process normally awaits for interruption from an input device in the user authenticating means while presenting a message expediting user authentication (step 601). As an input device, a keyboard, a mouse, an IC card reader, a fingerprint reading device, a voice pattern analyzing device, or a retina pattern photographing device is conceivable. Further, as data for inputting for authentication, there are used any one or more of a character string inputted from a keyboard, a mode of answering questions concerning information which is known only by a user per se by a mouse, a user identifier recorded on an IC card, a fingerprint, a voice pattern, a photographed retina pattern of the person. When an interruption is caused in executing step 601, the program is brought into a state transition and starts input reception (step 602). After obtaining data for authentication of the user by the above-described method, the operation makes a reference by using a registered user register list (step 603) and when the operation succeeds (step 604), the operation informs that the authentication has succeeded and the name of the user to the table control process (step 605). Information of various data among processes is carried out via a shared memory or a pipe. The shared memory signifies a memory area which can be referred to from a plurality of processes and the pipe signifies a mechanism used for transmitting data from one process to other process. These mechanisms are provided by OS. Although the following procedure is not illustrated, the table control process receives it and updates the user table. In accordance with updating the user control table, the device table is also updated. When there is a change in respect of a user who is using the apparatus, data in respect of the respective devices is also automatically updated.

Figure 7:
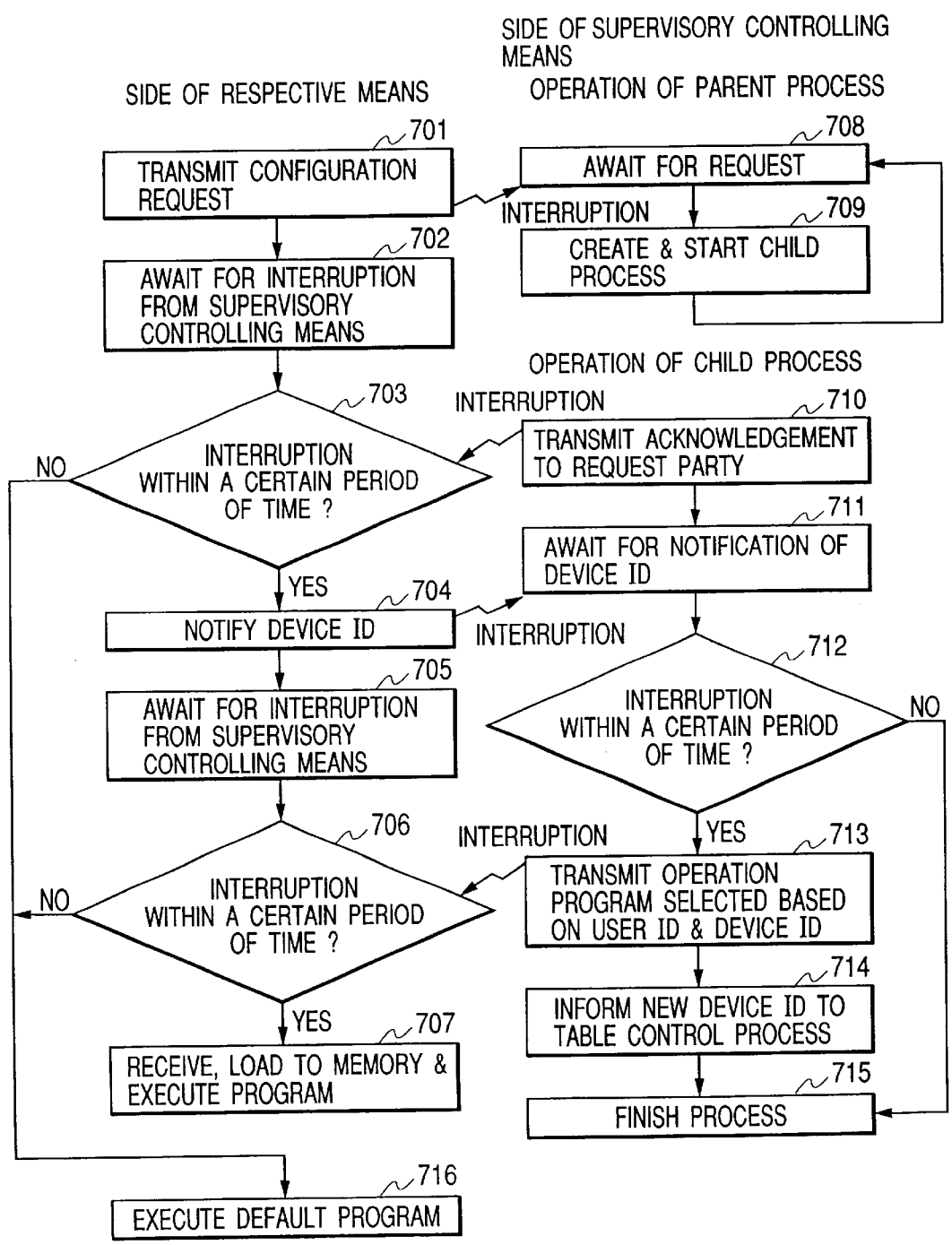
FIG. 7 is a diagram showing operation of a system configuration process.

Next, an explanation will be given of the system configuration process of the supervisory controlling means 126 in requesting configuration of respective means in reference to FIG. 7.

The system configuration process on the side of the supervisory controlling means 126 awaits for a request for configuration by interruption from respective means (step 708). An interruption is informed by interruption signal lines when the supervisory controlling means 126 and the respective means are coupled by various buses mentioned above. When they are coupled by a network, it is realized by socket communication designating port numbers. In this case, a request is transmitted from either of the respective means (step 701). The respective means make a request when there causes a situation of any of power source ON (start), reset, interchange of tools, a change in content of operation. A description will be given later thereof. By the interruption, the system configuration process is brought into a state transition from step 708 to step 709 and a child process for carrying out a processing in respect of the request is created and started (step 709). In this case, the child process is created and started to be able to deal with a case in which another configuration request is made from other respective means. A party of transmitting the request awaits for acknowledgement (acknowledgement for request) by interruption from the supervisory controlling means 126 (step 702). When there is no interruption in a constant period of time (step 703), the respective means determines that malfunction is caused in the supervisory controlling means 126 and executes an operational program of default created by the means per se (step 716). When the acknowledgement from the child process which has been created and started is informed by interruption (step 710), the side of the supervisory controlling means 126 awaits for notification of device ID from the respective means (step 711). The party of transmitting the request which receives the acknowledgement by interruption, carries out notification of device ID by interruption (step 704) and awaits for distribution of the operational program from the supervisory controlling means 126 (step 705). In this case, when distribution of the program via interruption is not carried out in a constant period of time, the request party executes an operation program of default owned by the party (step 716). The child process awaiting for notification of device ID finishes execution process as it is when the device ID is not informed by interruption in a constant period of time (step 715). In this case, the device table is not updated. When the device ID is notified by interruption from the request party, the child process reads an operational program selected based on the informed device ID and a user ID of a user who can currently use the device from the operational procedure description storing means 129 (when acquisition of data from portion 129 is failed for some reason, reads from inside of the supervisory controlling means 126) and distributes it to the request party via interruption (step 713). The request party receives the operational program upon reception thereof, records it to the operational procedure description recording and storing means 202 and executes it (step 707). The child process informs the new device ID to the table control process by means of a shared memory or the like mentioned above (step 714). Although not illustrated, a signal is transmitted in notification and makes the party notice that data is transmitted. The signal signifies a signal exchanged among processes and the mechanism is realized by intervention of OS. After carrying out the above-described operation, the child process is finished and disappears (step 715). As described above, child processes are created by a number of requests and accordingly, even when the plurality of requests are transmitted asynchronously from various places, they can be dealt with.

Figure 8:
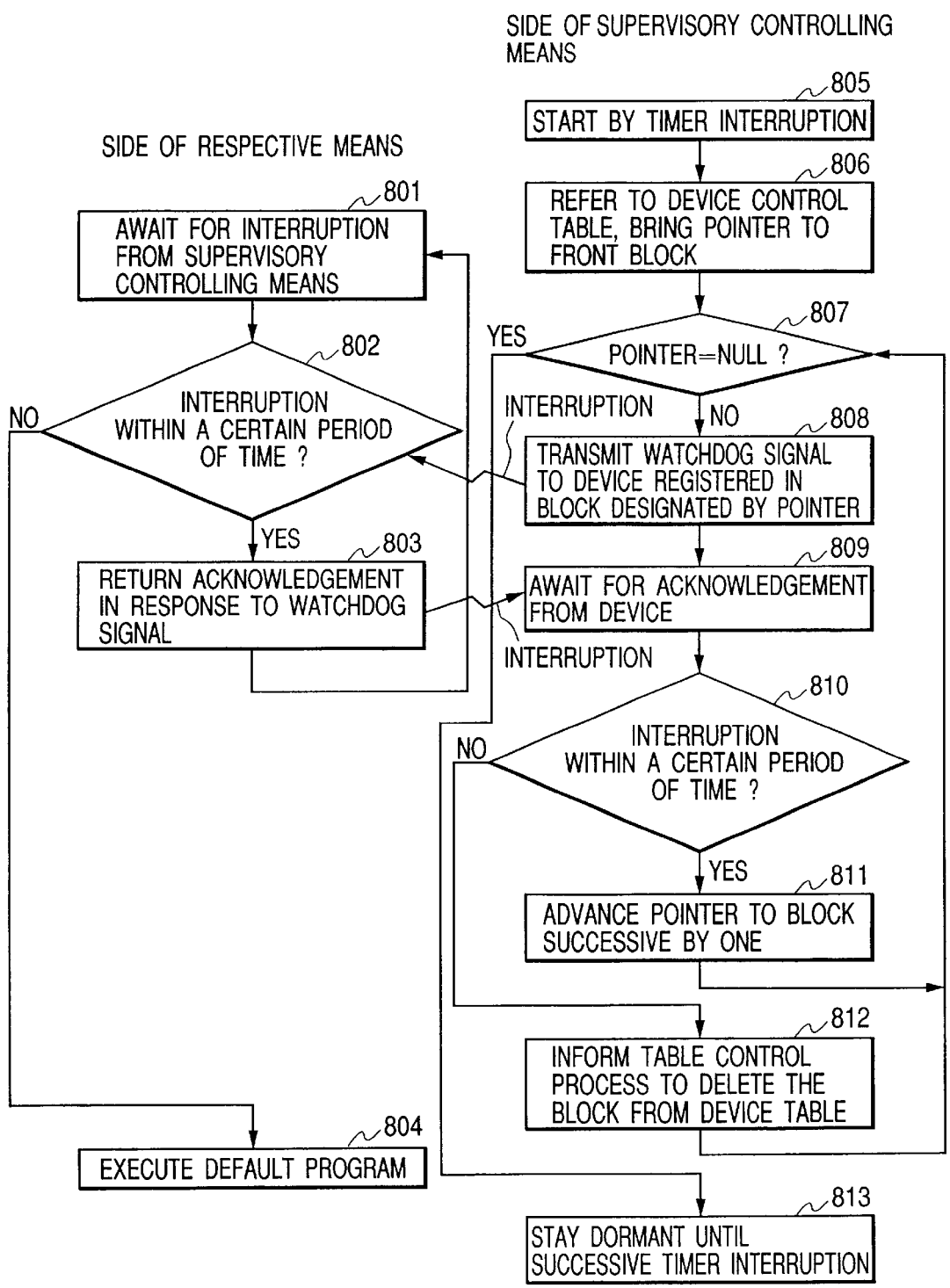
FIG. 8 is a diagram showing operation of a watch dog process and a program on a side of respective means.

Next, an explanation will be given of the watch dog process of the supervisory controlling means 126 and operation of program on the side of the respective means in correspondence therewith in reference to FIG. 8.

The process is periodically started by timer interruption and executed (step 805). Next, a reference is started from a front block (mentioned later) of the device table on the shared memory (step 806). A watch dog signal is transmitted to a device registered in a block which is being referred to currently (any of respective means) via interruption (step 808). Meanwhile, the device awaits for interruption from the supervisory controlling means 126 (step 801) and when there is no watch dog interruption in a constant period of time, the device determines that malfunction is caused in the supervisory controlling means 126 and switches to an operation program of default owned by itself (step 804). Otherwise, the device transmits acknowledgement (answer to watch dog) in response to the watch dog signal via interruption (step 803). The process awaits for acknowledgement from the device after transmitting the watch dog signal (step 809) and determines that the device has been extinguished for some reason when there is no interruption in a constant period of time and informs the table control process that the block of the device is to be deleted from the device table (step 812). The information in this case is carried out also by the above-described signal. When the acknowledgement is returned, the operation determines that the device exists and is operating and refers to a block in which a successive device is registered (step 811). In the device table, blocks registering devices constitute a linear list and a certain block stores a pointer to a successive block (address on memory). A pointer for a successive block in the final block points to NULL, that is, nothing. The user table is provided with a similar structure. A description will be given thereof later. As mentioned above, during a time period in which the pointer does not reach NULL, transmission of signal and standby for answer are repeated in respect to respective devices. When the reference has been finished in respect of a final portion of the linear list, the process pauses until starting by successive timer interruption (step 813). By the above-described operational procedure, operating states of the respective devices can always be monitored and the tables can be updated immediately when there causes a change.

Figure 9:
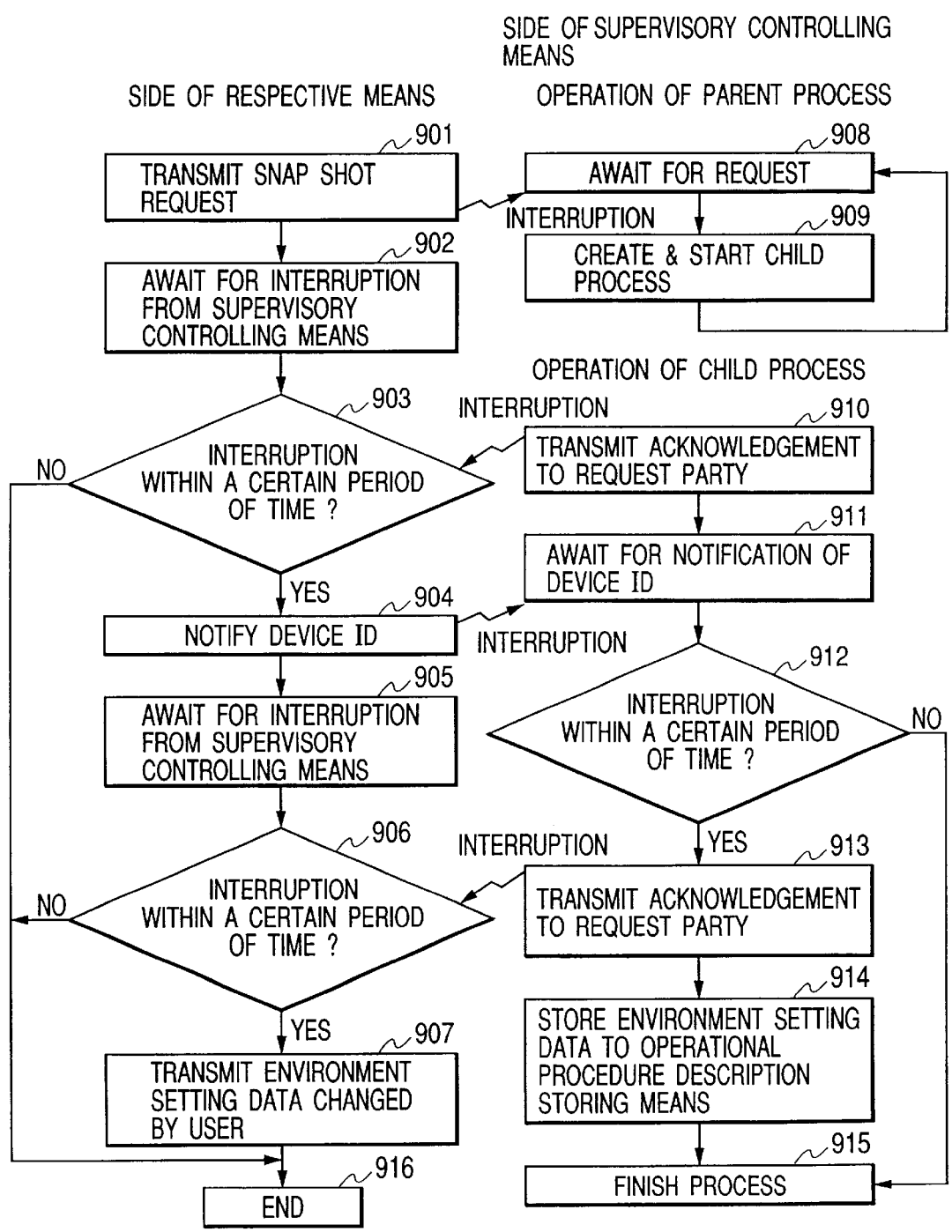
FIG. 9 is a diagram showing an operational procedure of a snap shot process.

Next, an explanation will be given of operational procedure of the snap shot process in reference to FIG. 9.

This realizes a function of the supervisory controlling means 126 for preserving states of the respective means, for example, when there causes environment setting data which a user changes during use in any of the respective means, the supervisory controlling means 126 preserves this. The snap shot process on the side of the supervisory controlling means 126 awaits for snap shot request from the respective means by interruption (step 908). Interruption is informed by interruption signal lines when the supervisory controlling means 126 and the respective means are coupled by the various buses mentioned above. When they are connected by a network, this is realized by socket communication designating port numbers. At this occasion, request is transmitted from any of the respective means (step 901). Timing of request is either or both of when there causes snap shot request from a user and at every constant time interval. The snap shot process is brought into a state transition from step 908 to step 909 by interruption and creates and starts a child process for carrying out a processing in respect of the request (step 909). In this case, the child process is created and started to be able to deal with a case in which snap shot request is transmitted from other respective means. A party of transmitting the request awaits for acknowledgement (acknowledgement in respect of request) by interruption from the supervisory controlling means 126 (step 902). At this occasion, when there is no interruption in a constant period of time (step 903), the respective means determines that malfunction is caused in the supervisory controlling means 126 and interrupts the processing (step 916). The side of the supervisory controlling means 126 notifies acknowledgement requested from the child process which has been created and started by interruption (step 910) and awaits for notification of device ID from the respective means (step 911). The party of transmitting the request which receives the acknowledgement by interruption, carries out notification of the device ID by interruption (step 904) and awaits for interruption of notification of the acknowledgement from the supervisory controlling means 126 (step 905). At this occasion, when the information of the acknowledgement via interruption is not carried out within a constant period of time, the party of the request interrupts the processing (step 916). Meanwhile, the child process awaiting for notification of the device ID finishes execution as it is when the device ID is not informed by interruption within a constant period of time (step 915). In this case, the environment setting data is not updated. When there is notification of the device ID from the party of the request by interruption, the child process transmits again the acknowledgement to the corresponding device via interruption (step 913). The party of request receives this and transmits the environment setting data which is changed by the user (step 907). The child process stores the transmitted environment setting data to the operational procedure description storing means 129 (step 914). After having executed the above-described operation, the child process is finished and disappears (step 915). Although not illustrated, the data is attached with tags by the device ID and the user ID and is treated as a portion of the operational procedure description, that is, a portion of transmitted program at a successive time and later. Child processes are created by a number of transmission of requests as described above and accordingly, the operation can deal with even a case in which a plurality of requests are transmitted a synchronously from various places.

Figure 10:
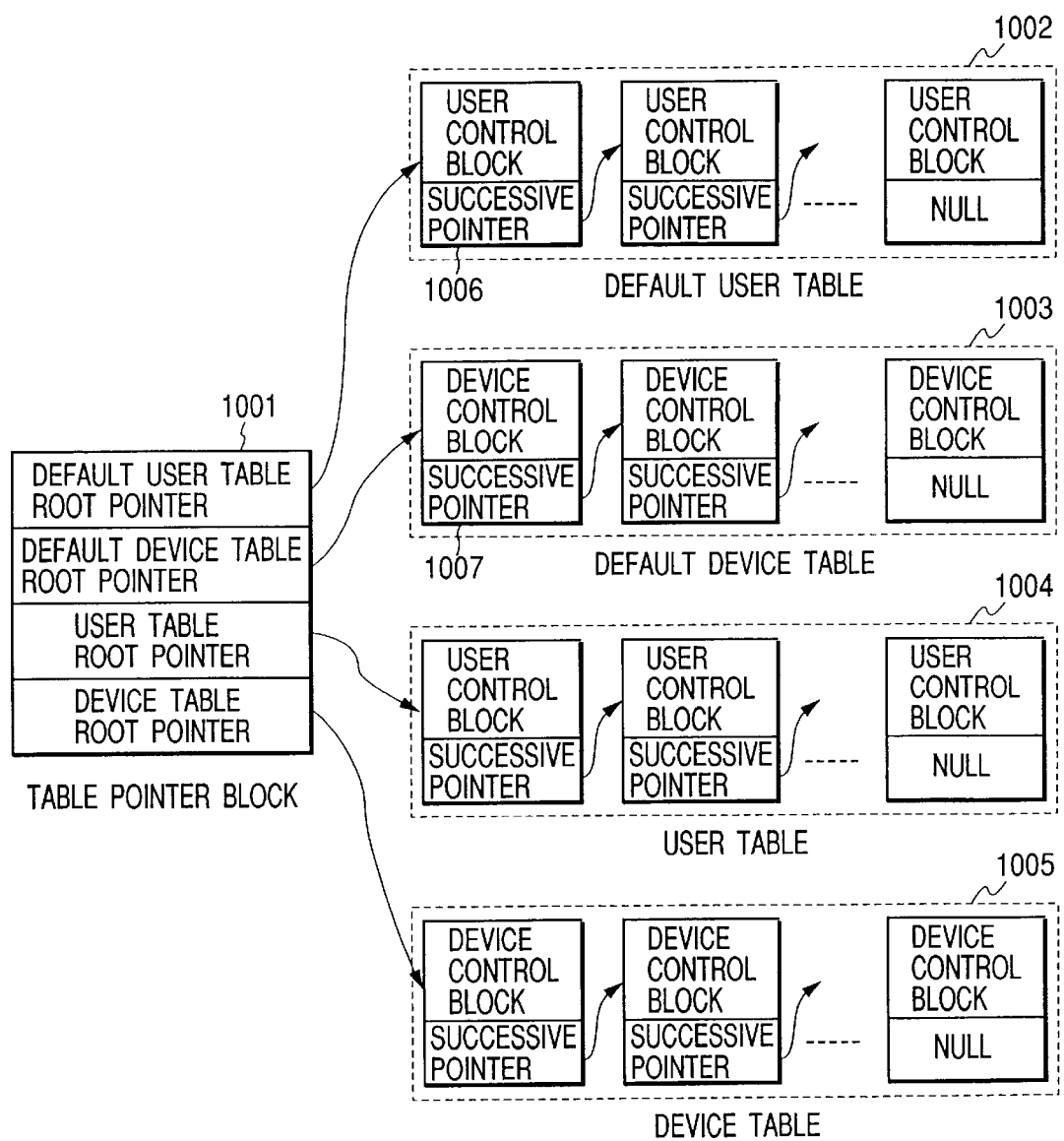
FIG. 10 is a diagram showing a data structure of a device table, a user table and a periphery thereof.

Next, an explanation will be given of the device table, the user table and data structure of the periphery in reference to FIG. 10.

Figure 11:
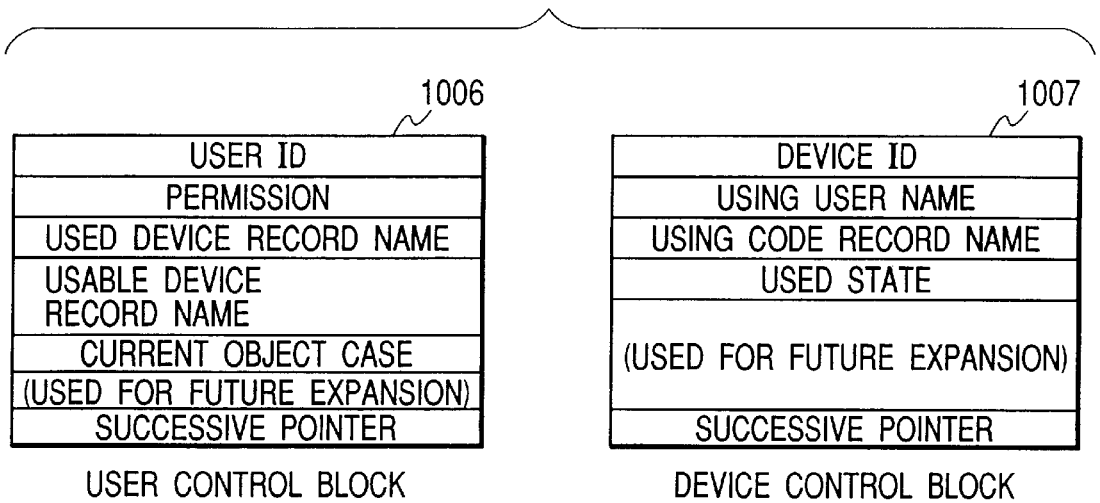
FIG. 11 is a diagram showing a data structure of a user control block and a device control block.

Numeral 1001 designates a table pointer block, numeral 1002 designates a default user table, numeral 1003 designates a default device table, numeral 1004 designates a user table, numeral 1005 designates a device table, numeral 1006 designates a user control block and numeral 1007 designates a device control block, respectively. A data area used therefor is dynamically provided in a memory of the supervisory controlling means by the table control process (not illustrated). The respective tables create linear lists as mentioned above and an address of a successive block is described in the block. Operation of addition and deletion of a block to and from the list can be realized by provision/release of a memory in the program and pointer operation. A detailed explanation will not be given here in respect of the pointer operation. The user control block 1006 is provided with a data structure as shown by FIG. 11. One block is constituted by user ID, permission indicating right of operation of the user in respect of a total of the system, name of used device record recording an identifier of a file stored with data of a device control block currently used, usable device record name and a current object case and there is a area at a final portion of the block for recording a successive pointer which is a pointer for a successive block. One block of the device control block 1007 is provided with device ID, name of user using the device, code record name on use which is an identifier of a file of an operation program which is being executed by the device, an area for recording a state of use of the device (using, awaiting for use, pausing) and finally, an area of recording a successive pointer which is a pointer for a successive block.

Figure 12:
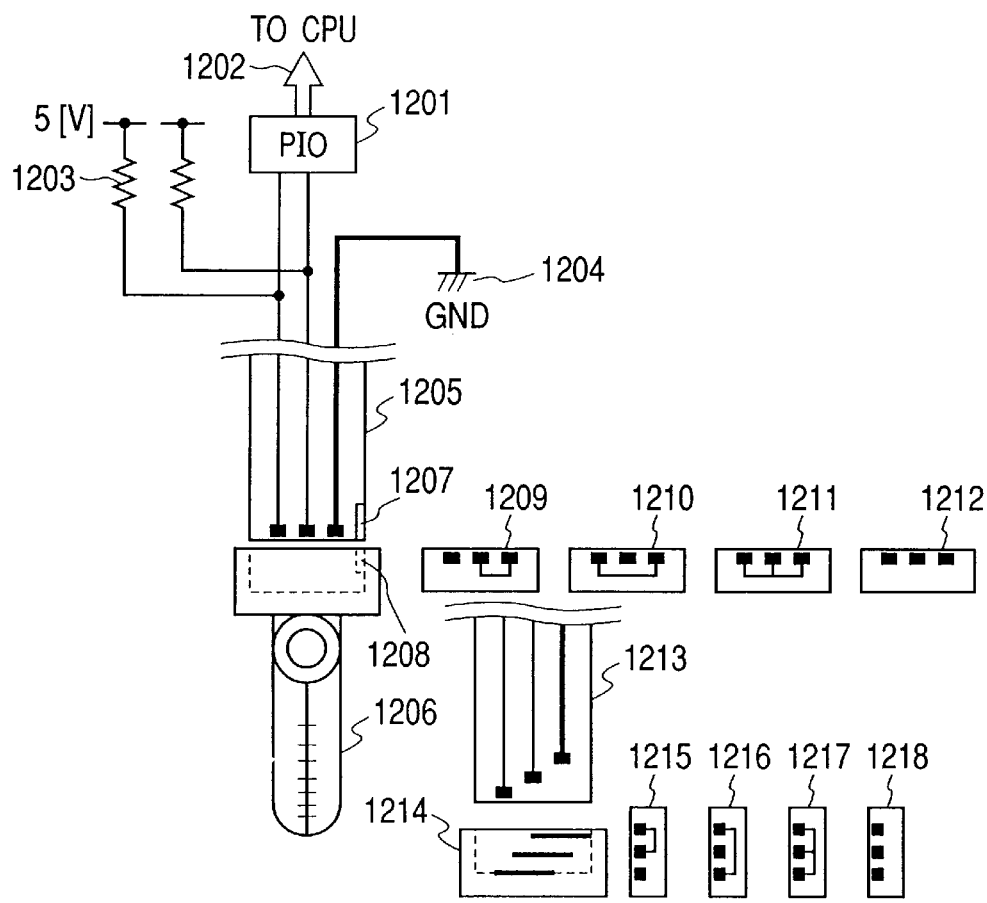
FIG. 12 is a diagram showing an example of a method of acquiring an intermediary order portion of device ID (Identification) in respective means.

Next, an explanation will be given of an example of a method of acquiring an intermediary order portion of device ID in respective means in reference to FIG. 12. There will be shown here an example of interchanging front end tools of a manipulator for operation.

Numeral 1201 designates PIO (Parallel Input/Output), numeral 1202 designates a bus to CPU (Central Processing Unit), numeral 1203 designates a pull-up resistor, numeral 1204 designates a reference potential point (ground), numeral 1205 designates a tip of a manipulator, numeral 1206 designates a tool attached to the manipulator, numeral 1207 designates a protrusion, numeral 1208 designates a notch, numerals 1209 through 1212 designate wiring patterns at an inner wall of a portion of fitting the tool, numeral 1209 designates pattern 1, numeral 1210 designates pattern 2, numeral 1211 designates pattern 3, numeral 1212 designates pattern 4, numeral 1213 designates other wiring pattern at a tip of a manipulator, numeral 1214 designates other wiring at the inner wall of the portion of fitting the tool, numerals 1215 through 1218 designate wiring patterns in respect of wirings of the portion 1214, numeral 1215 designates pattern 1 in respect of the portion 1214, numeral 1216 designates pattern 2 in respect of the portion 1214, numeral 1217 designates pattern 3 in respect of the portion 1214 and numeral 1218 designates pattern 4 in respect of the portion 1214. One end of the pull-up resistor 1203 is applied with potential of 5(V) and other end thereof is led to the tip of the manipulator via a lead wire. Lead wires are covered except portions of quadrangular pads. One of the lead wires communicates with the ground 1204. The tool 1206 is fittable always in a correct direction by the protrusion 1207 and the notch 1208. Wirings is carried out on the inner wall of the portion for fitting on the side of the tool such that electricity is communicated by various patterns between 5(V) and the ground. The wirings on this side are covered and insulated except portions of the quadrangular pads. In this case, there is shown an example in which 4 ways of identification is feasible by a pattern of 2 bits. For example, when right two pads are wired as in the portion 1209, in the case of fitting the tool, only a right side one of the pull-up lines is connected to the ground and accordingly, a pattern of 10 is constituted when a pattern of potentials of left and right pull-up lines is read by using PIO 1202. Similarly, 01 is constituted by the portion 1210 and 11 is constituted by the portion 1211. The portion 1212 designates a special pattern which is equal to a state in which the tool is not fitted when this pattern is connected. Accordingly, when a dummy tool wired with this pattern is fitted, it is regarded as equal to a state in which the tool is pulled off and accordingly, it can be recognized that the manipulator is not used. When the protrusion or the notch for fitting cannot be installed for some reason, the wiring at the tip of the manipulator is constituted as in the portion 1213, the wirings on the inner wall of the tool are constituted as in the portion 1214 and the wirings between these wirings are constituted as in the portions 1215 through 1218 by which bit patterns the same as the above-described can be produced. Further, in this case, only by fitting to the inner side, contact with wirings at a tip of a manipulator is always established within a range of rotation angle and accordingly, positioning in the rotational direction poses no problem. Further, although in the above-described example, bit patterns are produced by potential of respective wirings and are used as intermediary order of the device ID, this can be realized by combinations of optical fibers and wave guides or a fluid circuit.

Figure 13:
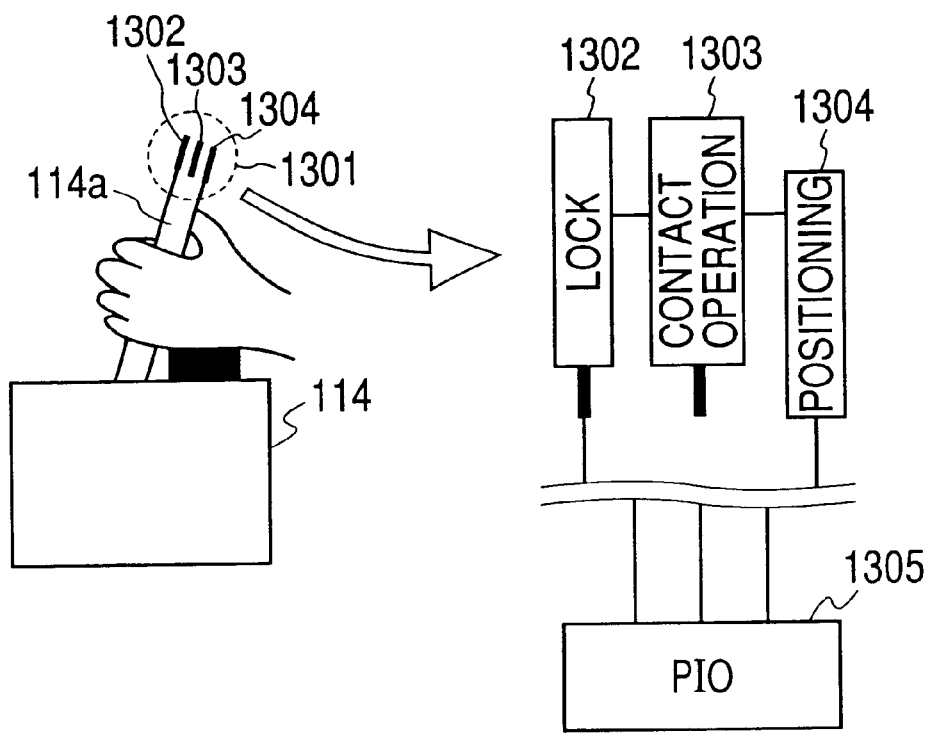
FIG. 13 is a view showing an example of a method of obtaining a lower order identifier of device ID.

Next, an explanation will be given of an example of a method of obtaining a lower order identifier of device ID in reference to FIG. 13.

Figure 14:
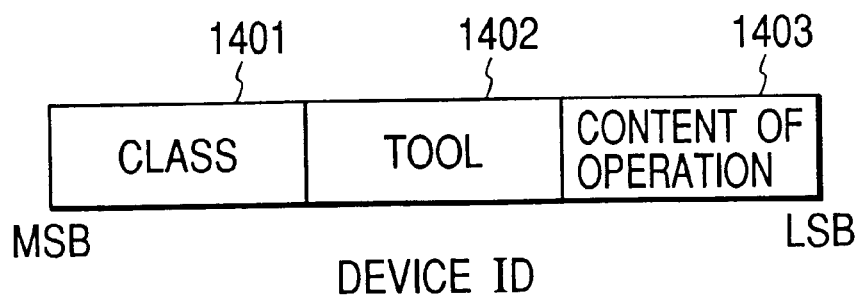
FIG. 14 is a diagram showing an example of a data structure of device ID.

The lower order identifier is used for expressing content of operation in respective means. FIG. 13 shows an example of designating content of operation of a manipulator for operation via the motion command inputting means 114. Numeral 1301 designates a group of switches for designating content of operation, numeral 1302 designates a switch designating lock for invalidating input of motion from a lever 114a, numeral 1303 designates a switch for designating contact operation for informing start of contact operation in respect of a diseased part to the system, numeral 1304 designates a switch designating positioning operation for informing start of positioning operation to the system and numeral 1305 designates PIO for detecting states of the switches. Although various kinds of operation are conceivable other than these such as a hybrid operation of position and force, these are not illustrated for simplifying explanation of the example. The above-described switches 1302 through 1304 are disposed above a movable portion in a cylindrical shape of the motion command inputting means. A user of the motion command inputting means 114 switches the above-described switches in accordance with operation to be executed. According to the switches, there is constructed a structure in which only any one of these can stay to be pushed down and when other one of the switches is pushed down, a previous one of the switches is returned to the original position. What switch is pushed down is detected through a method similar to that shown by FIG. 12. That is other method for detecting a line which is pulled up and a line which is not pulled up by PIO 1305. The kind of content of operation detected here is stored in the respective means and one device ID is constituted by combining it with the upper order and intermediary order identifiers mentioned above and is informed to the supervisory controlling means 126. FIG. 14 shows an example of a data structure of device ID. In this case, device ID is expressed by data having a certain bit width. Numeral 1401 expresses a class of a device, numeral 1402 expresses a kind of a tool and numeral 1403 expresses content of operation, respectively. As has already been explained, a class of a device expresses a general category of the device. Bit widths of respective orders are prepared to suffice to express types or kinds of a class, types of a tool and types of content of operation. For example, when kinds of classes are equal to or smaller than 16, a bit width necessary for the portion 1401 is 4. A bit width necessary for expressing a kind of a tool may express a maximum one of a number of kinds of tools in respective classes. For example, when a number of kinds of tools of a manipulator for operation is 7 and when this is a maximum number of pieces in all of the tools, the bit width for expressing the kinds of tools may be 3 bits at most. In respect of expression of content of operation, it is sufficient when a maximum value of number of kinds of content of operation can be expressed in the case where a certain tool is used in a certain class and accordingly, for example, when kinds of operation in the case of using a forceps tool by a manipulator for operation are 3 kinds of the above-described operation 1302 through 1304 and a number thereof is at maximum in all of combinations, a necessary bit width is only 2 bits at most. As mentioned above, a total bit width necessary for expressing device ID is 9 bits at most and is very small. Actually, addition of class, tool and content of operation is conceivable and accordingly, it is conceivable to provide allowance in respective bit widths, however, a change in the bit width for expressing the device ID per se is small since by increasing 1 bit, doubled kinds can be expressed. Further, the above-described switch may be, for example, a foot switch or of a style switched by voice or gesture.

Figure 15:
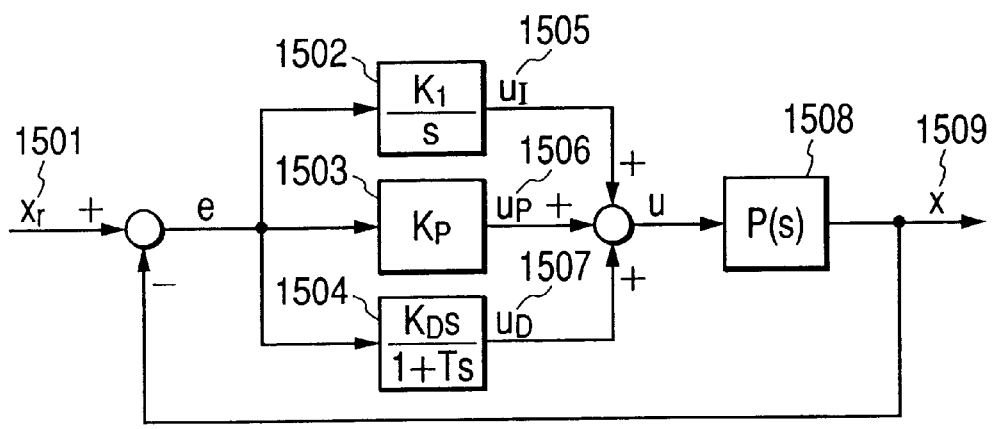
FIG. 15 is a diagram showing an example of a tip positioning control system in a positioning operation.
Figure 16:
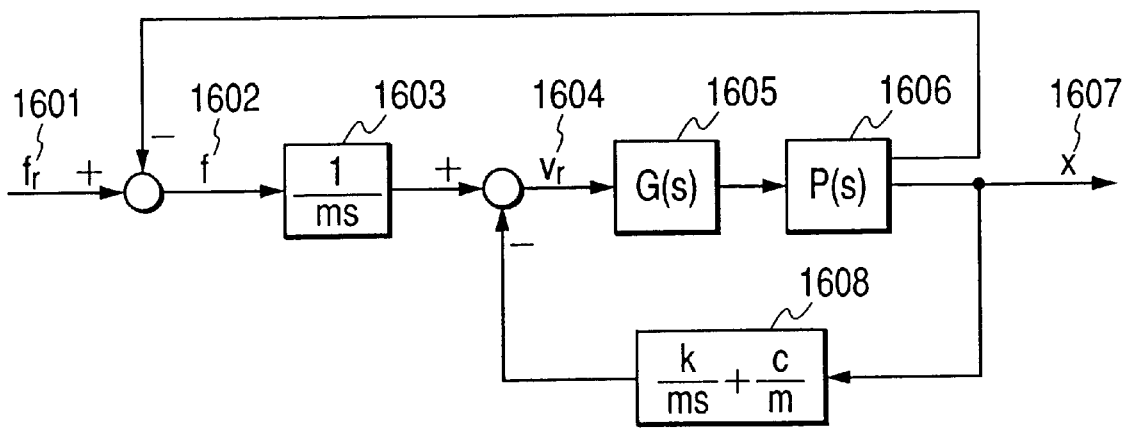
FIG. 16 is a diagram showing an example of a force control system in a touching operation of a manipulator.

Next, an explanation will be given of an example of an operation program which is redistributed by a change in a tool or content of operation in a certain means in reference to FIG. 15, FIG. 16, Equation 1 and Equation 2.

The following explanation shows an example of a case in which in a manipulator for operation, content of operation is changed and notified by the above-described method. The content of operation before change is positioning for controlling configuration of a tip of a pipe for injecting physiological salt water or configuration of a front end of optical fiber laser for burning to cut. Successively, in order to remove a tissue by forceps, interchange of tools and switching of operational content designating switches are carried out. FIG. 15 shows a control system indicating algorithm for tip positioning control in positioning operation. Although there are various methods in positioning control, in this case, an explanation will be given of an example of a PID (Proportional, Integral and Derivative) control system as a representative one. The control system is constituted in joint coordinates or operational coordinates. Numeral 1501 designates a position instruction value $x_r$ which is given from motion command inputting means in a normal case. Numerals 1502 through 1504 designate constituent elements of a compensator. Numeral 1502 designates an integral element in the compensator, numeral 1503 designates a proportional element and numeral 1504 designates a derivative element. Numerals 1505 through 1507 designate outputs provided by applying a deviation $e=x_r-x$ to respective elements and a total of these constitute control input u. Numeral 1508 designates a transfer function of a control object and the transfer function is inputted with u mentioned above. Numeral 1509 designates positional response of the control object P(s) as a result of inputting u. Although there are various methods of mounting the above-described control system, there is one way of making the control system discrete and describing the procedure in the form of calculation in a program. The control system of FIG. 15 is made discrete and described by equations to thereby constitute (1) through (5) of Equation 1.

$$e(t_k)=x_r(t_k)-x(t_k) \tag{1}$$

$$u_I(t_k)=u_I(t_{k-1})+t_sK_Ie(t_k) \tag{2}$$

$$u_p(t_k)=K_p e(t_k) \tag{3}$$

$$u_D(t_k) = \frac{1}{t_s+T}(Tu_D(t_{k-1}) + K_D(e(t_k) - e(t_{k-1}))) \tag{4}$$

$$u(t_k)=u_I(t_k)+u_p(t_k)+u_D(t_k) \tag{5}$$

where $t_k=k \times t_s$; $t_s$ designates sampling time (k=0, 1, 2 . . . ).

At sampling time $t_k$ at a k-th time, the deviation $e(t_k)$ between a target position and response is expressed by (1). This is given to respective elements of FIG. 15 and operation of providing compensating amounts $u_I$, $u_P$, $u_D$ is discretely expressed by equations (2) through (4) and the control input $u(t_k)$ at the time becomes a total of these.

Next, an operation program describing control algorithm necessary for carrying out contact operation is distributed by notifying interchange of tools and a change in content of operation and the operational program is executed. FIG. 16 shows an example of a typical force control system in contact operation of the manipulator. Numeral 1601 designates an reference (or desired) value of force, numeral 1602 designates force detected at the tip of the manipulator, numeral 1603 designates an integral element for expressing inertia, numeral 1608 designates an element for expressing viscosity and stiffness, numeral 1604 designates a velocity reference value for producing desired force at the tip of the manipulator, numeral 1605 designates a compensator for realizing the given velocity reference value in a control object, numeral 1606 designates the control object and numeral 1607 designates position response of the control object. A general equation model of the force control system is expressed by (6) of Equation 2.

$$f_r-f=mx+cx+kx \tag{6}$$

$$v_r = \frac{1}{m}\int (f_r - f)dt - \frac{c}{m}x - \frac{k}{m}\int x dt \tag{7}$$

$$\Rightarrow$$

$$v_r(t_k) = v_r(t_{k-1}) + \frac{1}{m}(t_s(f_r(t_{k-1}) - f(t_{k-1})) - (c - t_s k)x(t_{k-1}) + cx(t_{k-2})) \tag{8}$$

By modifying (6), velocity reference is obtained as shown by (7). By making the equation discrete, equation (8) for providing velocity reference at time $t_k$ is obtained. A calculation for expressing (8) is described in the redistributed operation program. Thereby, the user can execute contact operation by using the manipulator which has executed positioning operation before interchanging tools without changing the program by the user per se and without being conscious of the change. Such a change in the content of operation cannot be dealt with simply by change of parameters of the control system but needs a change in the operation program per se such as control algorithm. When a program is described such that algorithms can be selected, the program size is enlarged and more of resources (memory, disk) for executing the program is needed and accordingly, the cost is increased. Further, algorithm which is not described in the program cannot be used and an improvement in algorithm cannot be expected. Meanwhile, according to a mechanism of distributing a program from outside of respective means as described in the specification, operation program describing algorithm as needed or the same algorithm which is improved in minute portions can be utilized and accordingly, the respective means can achieve a maximum performance always at the time point.

Figure 17:
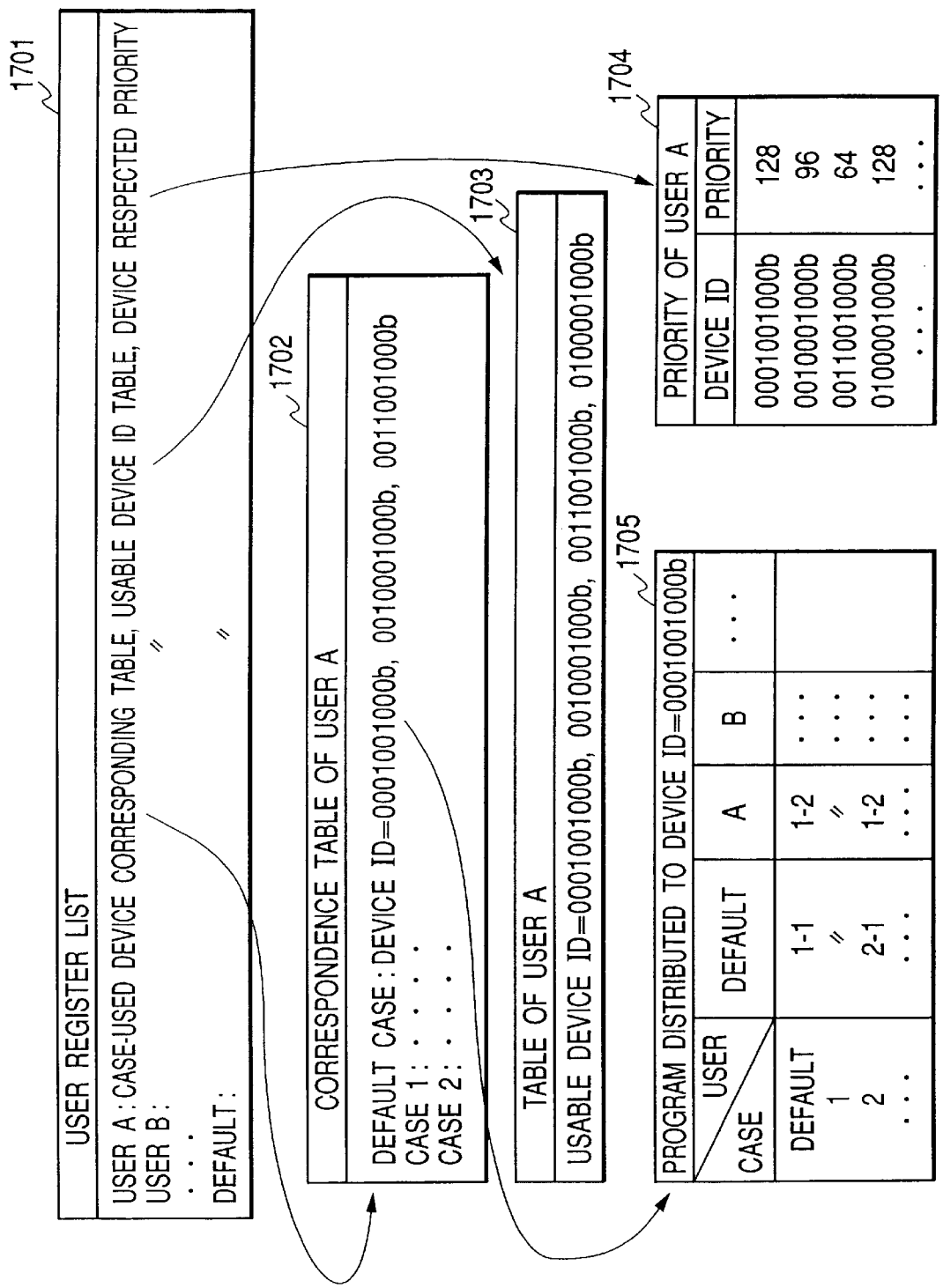
FIG. 17 is a diagram showing an example of a relationship between a user register list and various table data.

Next, an explanation will be given of an example of a relationship between a user register list and various table data in reference to FIG. 17.

Numeral 1701 designates a user register list, numeral 1702 designates a table of correspondence between object cases and used device IDs in respect of a user A, numeral 1703 designates a device table the use of which is permitted to the user A, numeral 1704 expresses operation priority in respect of devices usable by the user A and numeral 1705 designates a table of correspondence among users, object cases and distributed programs in respect of device ID=0001001000b, respectively. The data is stored in the operational procedure description storing means 129 and, held also in the supervisory controlling means 126 as backup. The both differ from each other in that only the former is updated when a snap shot is taken in operating the system. Although the latter is copied and updated from the former when the system is started, it stays unupdated during a time period of operating the system. The user register list 1701 is recorded with data concerning registered users. Names of files recorded with the case-used device ID correspondence tables and the usable device ID tables ("usable" in this case signifies presence of right of use) and priorities for respective usable IDs are described concerning respective users and default users. The priority indicates with how much priority a certain user can use a certain device. When a usable device is duplicated in respect of a plurality of users using thereof, a person having a higher priority is provided with right of operation. Numeral 1702 indicates an example of the case-usable device ID correspondence table concerning user A.

IDs of used devices are recorded for every case. Further, numeral 1703 designates the usable device table of user A. It is recorded with device IDs usable by user A. Usable devices in respect of respective cases of the table 1702 must be included in the table 1703. The table 1704 is recorded with priorities in respectives of usable devices IDs described in the table 1703. The table 1705 is stored with a table for determining a program for distributing by regarding a combination of a case and a user in respect of a device of a certain device ID. Numerals 1-1, 1-2 and so on in the table 1705 designate file names of programs to be distributed. The operational procedure description storing means 129 needs not to necessarily summarize under one computer or file system. Accordingly, in this case, the file name may be added with a name of a machine and a directory. In accordance with the file name, the supervisory controlling means 126 carries out operation of storing the above-described data as data base, updating it as necessary and ensuring consistency of content. "Permission" in the portion 1006 of FIG. 11 designates the device respective priorities 1704 or an item designating thereof (file name or the like). As the used device record name, the file name of the table 1702 is described and a list of device IDs in correspondence with a current object case is provided. Thereby, the device control blocks 1007 in the device table are created by a number of device IDs in the list. A device ID field is recorded with device ID and the name of a using user is recorded with user ID. The using code record name is provided by referring to a user control block from the name of a using user and referring to the table 1705 by object cases, the above-described user name and device ID. A usable device record name is described with the file name of the table 1703. Correspondence between case and used device ID is of a current state confirming type and when a user carries out addition, interchange or removal of a device in the midst of surgical operation, snap shot request is transmitted from the respective means to the supervisory controlling means 126 and the table control process updates the table 1702 based on the data. Further, in respect of content of respective data base of FIG. 17, a change in the content can separately be carried out and only the system administrator is provided with right of changing the data base. However, the system administrator may be one of users. This is realized by file control function of OS (setting access right) operating in the supervisory controlling means 126. However, only in respect of the corresponding table 1702 as mentioned above, the data base is updated automatically or under instruction of a user, mentioned later, to reflect a constitution changed by the user in the surgical operation.

Figure 18:
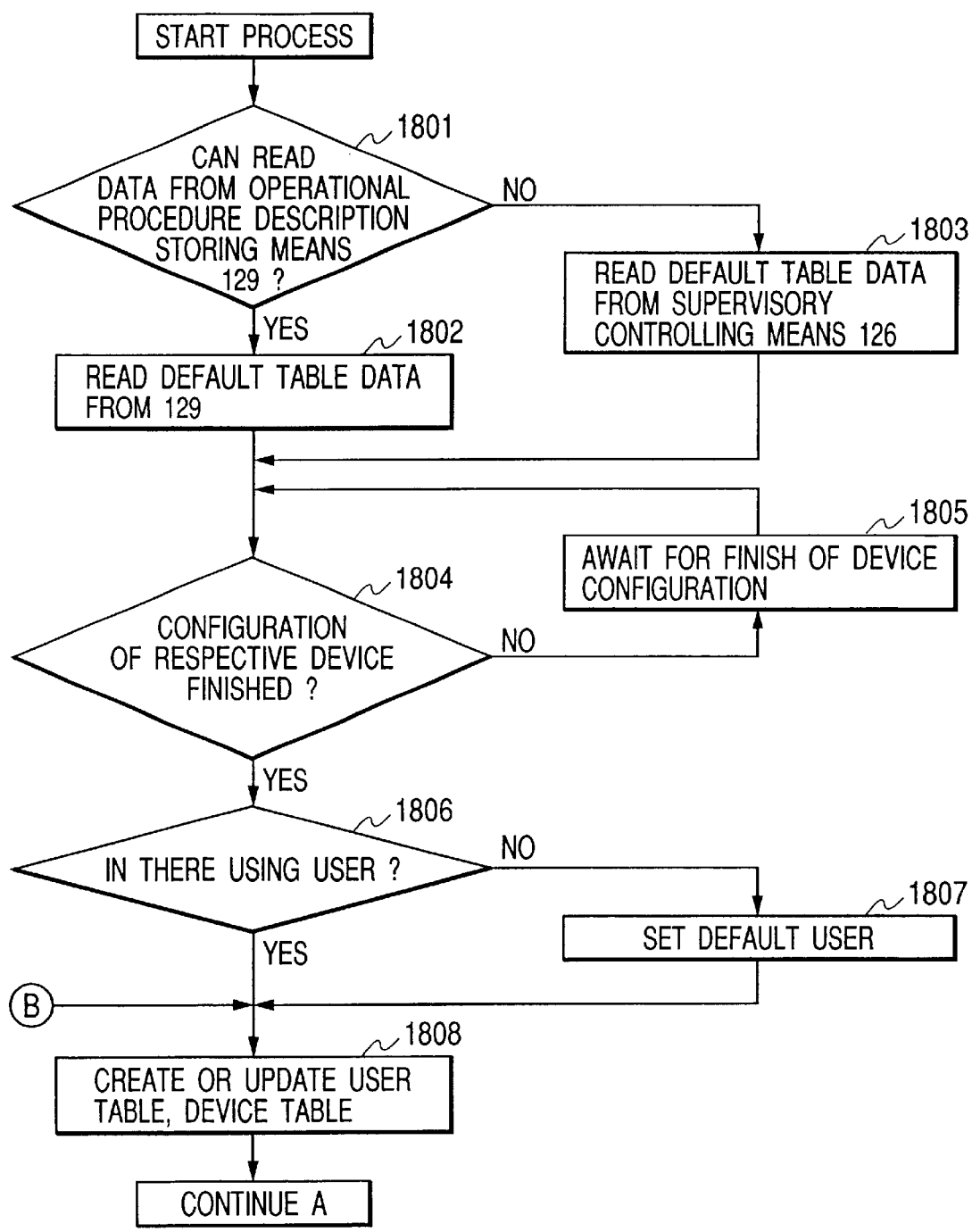
FIG. 18 is a diagram showing an operational procedure 1 of a table controlling system.
Figure 19:
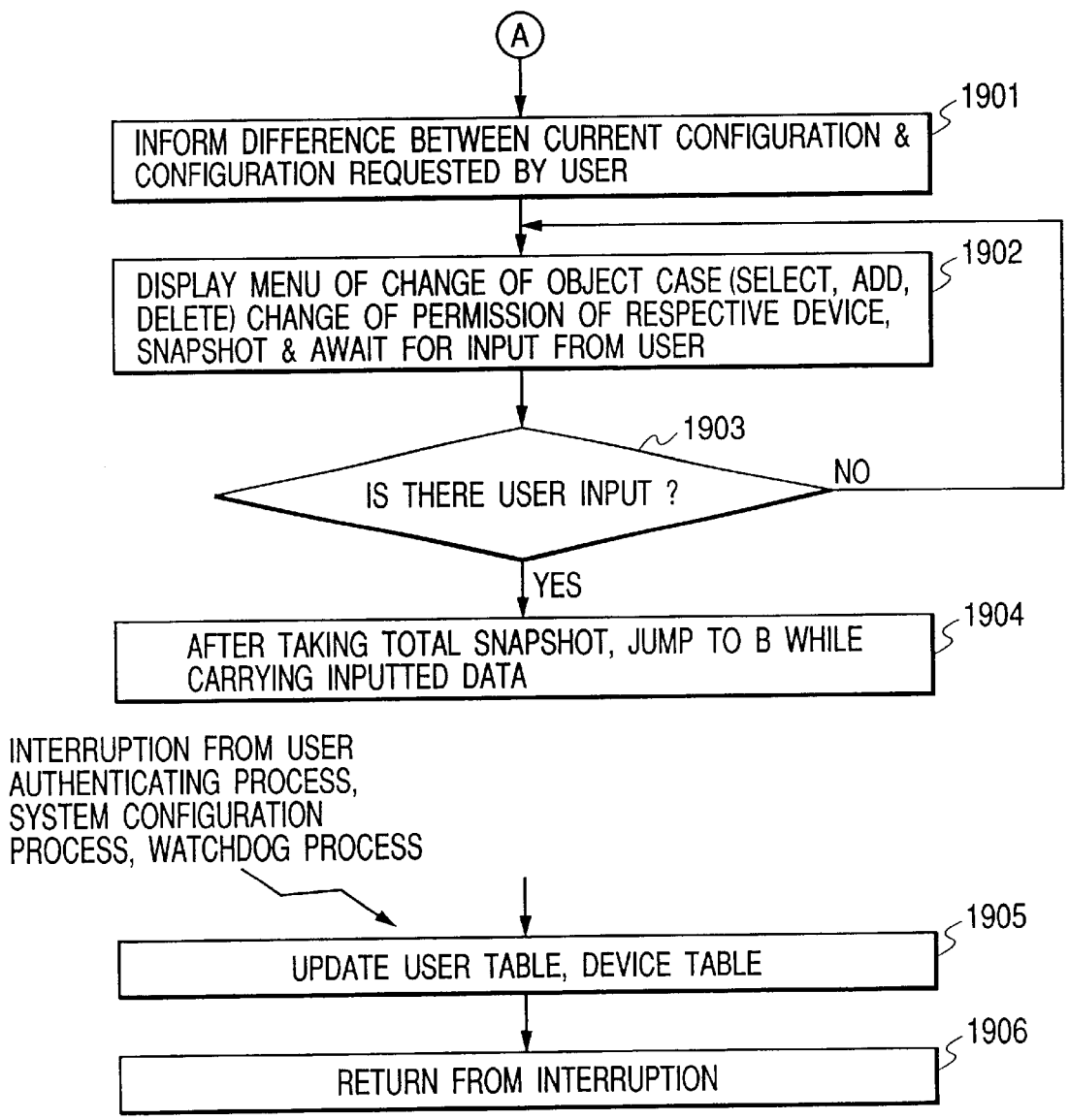
FIG. 19 is a diagram showing an operational procedure 2 of the table controlling system.

Next, an explanation will be given of an operational procedure of the table control process in reference to FIG. 18 and FIG. 19.

The process confirms that table data of default can be read from the operation procedure description storing means 129 (step 1801) and copies data necessary for creating the table of default from the operational procedure description storing means 129 onto the memory when it is readable (step 1802). In this case, although the using user cannot be utilized in referring to the data base for creating the table, actually, not so much difference is caused between the table of default and the table inherent to the user and accordingly, new reference of data is not caused so much also in modifying operation, mentioned later. When the data base of the operational procedure description storing means 129 cannot be referred to for some reason of malfunction of the operational procedure description storing means 129 or the transmission path 128, backup data in the supervisory controlling means 126 is read (step 1803). Next, completion of configuration of device is awaited for (step 1804, step 1805). Next, a using user is investigated (step 1806) and when nobody is using, a user of default is set (step 1807). Next, data base based on the user ID (using user ID or default user ID) is referred to again, the previously created device table is modified and the user table is created or updated (step 1808). Further, there is informed a difference between a current configuration (list of device IDs present in the system) and a configuration requested by a user (list of used device IDs. Immediately after having been authenticated by a user, a case is default. When a case is designated by a menu, mentioned later, list of device IDs in correspondence with the case) (step 1901). However, the side of a system does not carry out operation of resolving the difference and the handling is entrusted to the user. When some of devices to be used by a user in a certain case are not present in the current system, addition of devices or depletion of IDs of the devices which are not present from the list is not carried out at the system's own discretion. Action of resolving the difference persistently by the user is carried out in the surgical operation. As an example, there is conceivable a case in which when a surgeon preferring to a method of operation using a celiac wall hanging apparatus in a celiac operation, is going to carry out surgical operation by using a surgical apparatus, the supervisory controlling means 126 informs the surgeon that a manipulator for hanging up the celiac wall is not connected as a constituent element of the surgical apparatus which the surgeon is going to use actually. By being informed of the above-described fact, the surgeon can immediately take action of resolving the problem. That is, the surgeon arranges the manipulator from somewhere and connects it to the surgical apparatus. After the connected manipulator has been immediately recognized by the above-described procedure, distribution of an operation program depending on the surgeon who is a user is received and the apparatus becomes usable. Further, depending on cases, there can be caused a case in which the manipulator cannot be arranged to the site of operation. In this case, the surgeon makes decision of dispensing with the manipulator or stopping the surgical operation per se by himself or herself and in the case of dispensing with the manipulator, the surgeon instructs this to the supervisory controlling means 126. Only after receiving the instruction, the supervisory controlling means 126 deletes a block stored with data of the device from the list of device IDs. It is the proper method to entrust the decision to the user since the system per se does not and cannot execute action of actually bringing the device and physically connecting it. After having executed the above-described processing, the process displays a menu and awaits for input from the user (step 1902, step 1903). The menu shows a change in object case, temporarily change in operational permission for respective device or total snap shot request. The change in object case includes new selection, addition of new case or deletion of case. The temporary change in operational permission is used in the following case. That is, a case in which in respect of a certain device, a user having higher operational priority temporarily concedes right of operation to a user having lower operational priority. In this case, using user name and using code record name in the device control block of device ID are rewritten. The total snap shot is not snap shot of data for respective devices which is automatically requested by respective means as in interchanging devices but snap shot in respect of all of data in the user table and the device table. However, an amount of transmitted data is not so much large since it is updating operation only with respect to a changed portion. When there is input, the total snap shot (at time point at which input at the above-described step has not been yet reflected) is taken and the operation jumps to B of FIG. 18 while carrying inputted data (step 1904). In the above step, the menu to a user is presented by using computer display or additional voice guide. As a method of inputting by a user, there may be used text input from a keyboard, input by using GUI (Graphical User Interface) and a mouse, voice instruction or gesture. There is provided a step which is executed by making a change in respect of the tables by operation of other process separately from the above-described step and informing it. When there causes interruption request by signal or the like from the above-described user authenticating process, system configuration process or watch dog process, the process transits to a processing in correspondence with interruption. In the interruption processing, the operation carries out updating of a user table and a device table (step 1905) and thereafter returns from the interruption to a position of executing the original program (step 1906).

By the above-described constitution, there can be provided a surgical apparatus by which a user can constitute respective means such that they can be easily used by himself or herself and which is capable of continuing to use with the highest function without being troubled with readjustment even in the case in which the constitution is changed in using the apparatus.

What is claimed is:

1. A surgical apparatus comprising:

a plurality of devices respectively having controlling means including devices comprising operational manipulators for operating tools used in a surgical operation;

motion command inputting means for commanding motions of the devices for operating the tools;

supervisory controlling means having communicating means among the plurality of devices for supervisory controlling the devices; and operational procedure description storing means for storing an operational procedure description describing operational procedures of the plurality of devices;

wherein the supervisory controlling means includes detecting means for detecting constitutions of the devices and transmits the operational procedure description in conformity with the constitutions of the devices detected by the detecting means to the respective devices by the communicating means.

2. The surgical apparatus according to claim 1, wherein the detecting means detects at least one of the presence or absence of use of the devices, tools provided to the devices and contents of operations of the devices as the constitutions of the devices.

3. The surgical apparatus according to claim 1:

wherein when a power source is inputted to the surgical apparatus or is reset, the detecting means detects the constitutions of the devices by a request from the device to supervisory controlling means by an interruption.

4. The surgical apparatus according to claim 1:

wherein when a change is caused in the constitutions of the devices, the detecting means detects the constitutions of the devices by a request from the device to the supervisory controlling means by an interruption.

5. The surgical apparatus according to claim 1:

wherein the devices are provided with operational procedure descriptions of default and executes the operational procedure descriptions of default when the operational procedure descriptions are not transmitted from the supervisory controlling means.

6. The surgical apparatus according to claim 1, further comprising:

authenticating means for authenticating a user; and wherein the supervisory controlling means sets priorities of using the devices in respect of a plurality of users.

7. The surgical apparatus according to claim 1, further comprising:

authenticating means for authenticating a user; and wherein the supervisory controlling means determines priorities provided to a plurality of the users in respect of using the devices and transmits the operational procedure description of the device prepared for one of users having the highest priority to the device by the communicating means.

8. The surgical apparatus according to claim 3, further comprising:

means having data in respect of the constitutions of the devices of default with regard to a case for presenting a difference between the constitutions of the devices of default and constitutions of actually set ones of the devices.

9. A surgical apparatus for supporting surgical operators in carrying out a surgical operation by remotely controlling an operating tool or a curer, said surgical apparatus comprising:

motion command inputting means for commanding motions caused by respective surgical operators;

operational instruction creating means for converting motion command outputted from the motion command inputting means into operational instruction data;

diseased part tissue operating means for interpreting the operational instruction from the operational instruction creating means, carrying out a positioning operation in respect of a diseased part and generating one kind or more of kinetic energy, optical energy, electrical energy and thermal energy to thereby deform, destruct and modify the tissue;

work environment data detecting means for detecting image data of an operated portion and approach and a contact force of the diseased part tissue operating means to the diseased part;

in vivo data measuring means for applying one kind or more of a varying magnetic field, an electromagnetic wave and an ultrasonic wave to the diseased part and a surrounding thereof and measuring a passed-through or resonant signal;

measuring data processing means for reconstructing a signal measured by the in vivo data measuring means successively into a three-dimensional measured data image;

realism control data creating means for synthesizing and presenting to the respective surgical operators outputs from the measured data processing means and the work environment data detecting means;

user authenticating means for authenticating users permitted to carry out the operation;

operational procedure description storing means for storing a description of operational procedures interpreted and executed by respective means; and supervisory controlling means for supervisorily controlling the respective means;

wherein the supervisory controlling means transmits the description of the operational procedures from the operational procedure description storing means to the respective means in accordance with the users or object cases or constitutions of the respective means and transmits from the operational procedure description storing means to the respective means the description of the operational procedures after a change in the users or the object cases or the constitutions of the respective means in the surgical operation in accordance with the change.

10. A surgical apparatus used in a surgical operation, said surgical apparatus comprising:

devices having controlling means;

supervisory controlling means having communicating means among the devices; and operational procedure description storing means for storing an operational procedure description describing operational procedures of the devices;

wherein the supervisory controlling means includes detecting means for detecting constitutions of the devices and for transmitting the operational procedure description in conformity with the constitutions of the devices detected by the detecting means to the respective devices by the communicating means; and wherein the devices are provided with operational procedure descriptions of default and executes the operational procedure descriptions of default when the operational procedure descriptions are not transmitted from the supervisory controlling means.

11. A surgical apparatus used in a surgical operation, said surgical apparatus comprising:

devices having controlling means;

supervisory controlling means having communicating means among the devices; and operational procedure description storing means for storing an operational procedure description describing operational procedures of the devices;

wherein the supervisory controlling means includes detecting means for detecting constitutions of the devices and for transmitting the operational procedure description in conformity with the constitutions of the devices detected by the detecting means to the respective devices by the communicating means; and means having data in respect of the constitutions of the devices of default with regard to a case for presenting a difference between the constitutions of the devices of default and constitutions of actually set ones of the devices.

* * * * *